(12) United States Patent
Park et al.

(10) Patent No.: US 6,552,035 B2
(45) Date of Patent: Apr. 22, 2003

(54) COMPOSITION FOR INDUCING SMOKING CESSATION COMPRISING ALKALOIDS FROM *RADIX IPECAUANHAE*

(75) Inventors: Hwa-Mok Park, Seoul (KR); Byung-Zun Ahn, Taejeon (KR)

(73) Assignee: Hwa-Mok Park, Seoul (KR)

( * ) Notice: Subject to any disclaimer, the term of this patent is extended or adjusted under 35 U.S.C. 154(b) by 0 days.

(21) Appl. No.: 09/950,704

(22) Filed: Sep. 13, 2001

(65) Prior Publication Data

US 2003/0054051 A1 Mar. 20, 2003

(51) Int. Cl.[7] ............................................. A61K 31/44
(52) U.S. Cl. ....................... 514/294; 514/290; 514/299
(58) Field of Search ............................... 514/290, 299, 514/294

(56) References Cited

U.S. PATENT DOCUMENTS 4,139,589 A * 2/1979 Beringer et al.

FOREIGN PATENT DOCUMENTS

WO  WO 8909049  * 10/1989

OTHER PUBLICATIONS

Itoh et al., Tennen Yuki Kagobutsu Toronkai Koen Yoshishu (1999), 41st, 367–372 (abstract, Accession No.: 1999:776471 Caplus).*

Suzuki et al., Byoin Yakugaku (1989), 15(1), 1–4 (abstract, Accession No.: 1989:412575 Caplus).*

Itoh et al., Tennen Yuki Kagobutsu Toronkai Koen Yoshihu (1999), 41st, 367–32 (abstract, Accession No.: 1999:776471 Caplus).*

Suzuki et al., Byoin Yakugaku (1989), 15(1), 1–4 (abstract, Accession No.:1989:412575 Caplus).*

Goodman & Gilman's The Pharmacological Basis of Therapeutics, Ninth Edition; McGraw–Hill, Health Professions Division, 1996.

Deutsches Arzneibuch (German Pharmacopeia) pp 916–921 (English Abstract) Aug. 1986.

Gehard Madaus; Lehrbuch der biologischen Heilmittel; 1976; Georg Olms Verlag; pp. 1627–1635 (English Absract).

British Herbal Pharmacopoeia, Part Two; 1979; British Herbal Medicine Assoc. pp. 49.

* cited by examiner

*Primary Examiner*—Sreeni Padmanabhan
*Assistant Examiner*—S. Jiang
(74) *Attorney, Agent, or Firm*—Birch, Stewart, Kolasch & Birch, LLP

(57) ABSTRACT

This invention relates to a composition for inducing smoking cessation comprising as active ingredient alkaloids from *Radix ipecauanhae*. In smoking cessation program using the composition, the considerable number of volunteers participated in the program became nausea and thus ultimately to have no craving for smoking.

12 Claims, No Drawings

COMPOSITION FOR INDUCING SMOKING CESSATION COMPRISING ALKALOIDS FROM *RADIX IPECAUANHAE*

TECHNICAL FIELD

This invention relates to a composition for inducing smoking cessation comprising as active ingredient alkaloids from *Radix ipecauanhae*. More specifically, it relates to a composition comprising as active ingredient basic alkaloid fraction from *Radix ipecauanhae* or basic emetine, optionally in combination with one or more auxiliary agents selected from *Nicotiana tabacum*, Fructus Phyllanthus emblica, *Herba adenophorae, Herba leonuri, Herba foeniculi, Folia valerianae, Herba centellae* or *Circii herba*. The invention also provides a method for using the same.

BACKGROUND ART

*Nicotiana tabacum* contains harmful ingredients to human body such as nicotine, tar, dioxin and the like in large quantities. It is a one's favorite known to increase incidence of diseases related lung and cancers through long-term smoking. Various kinds of smoking cessation medicines or aids have been hitherto developed for smoking cessation. However, they have frequently adverse effects on human body or fail to successfully induce smoking cessation. Accordingly, it is absolutely needed to develop more efficient smoking cessation method or smoking cessation aid.

*Radix ipecauanhae*, as emetic, has been used for detoxification and the treatment of dysentery, and used as expectorant, depending upon its dosage (Deutsches Arzneibuch, British Herbal Pharmacopoeia, Gerhardt Madaus's Lehrbuch der Biologischen Heilmittel, Georg Olms 1976). However, it has never been used for inducing smoking cessation.

DISCLOSURE OF THE INVENTION

The present inventors carried out extensive studies to develop a novel efficient smoking cessation composition. As a result, they found that basic alkaloid fraction from *Radix ipecauanhae* of its constituent emetine can efficiently induce smoking cessation after various clinical trials and thus, completed the present invention.

Accordingly, a purpose of the present invention is to provide a composition for inducing smoking cessation comprising basic alkaloid fraction from *Radix ipecauanhae* or emetine as active ingredient.

Another purpose of the present invention is to provide the composition comprising basic alkaloid fraction from *Radix ipecauanhae* or emetine as active ingredient for smoking cessation, in combination with one or more selected from *Nicotiana tabacum*, Fructus Phyllanthus emblica, *Herba adenophorae, Herba leonuri, Herba foeniculi, Folia valerianae, Herba centellae* or *Circii herba*.

In the composition of the present invention, alkaloid extract from *Radix ipecauanhae* (root of *Cephaelis ipecacuanha*), an emetic, is used as active ingredient. *Radix ipecauanhae*, one species of Rubiaceae, is known as emetic and anti-dysentery. *Radix ipecauanhae* contains 1.9–2.1% of total alkaloids (Deutsches Arzneibuch 9, Edition 1986; British Herbal Pharmacopoeia 1979). Emetine (6,7,10,11-tetramethoxyemethan) and cephaelin are main ingredients in the alkaloid fraction. In the present composition, ipecac extract is used in the form of basic alkaloid fraction or emetine.

A mechanism that emetine will induce vomiting is as follows: it stimulates gastrointestinal system thereby to transduce signal to 5-$HT_3$ (5-hydroxytryptamine-receptor) in chemo-receptor trigger zone of area postremia and solitary tract nucleus. Subsequently, the transduced signal stimulates vomiting center in Medulla oblongota and then, passes through nervus vagus, phrenic nerve and abdominal muscular nerve to reach nausea followed by vomiting (Goodman & Gilman, The Pharmacological Basis of Therapeutics, 9th Edition, 1996).

Alkaloids in *Radix ipecauanhae* are usually in the form of salt with acid and commercial emetine is emetine hydrochloride. If smoking this salt as is, acidic moiety will transform to gaseous acid to have harmful effects on oral cavity, bronchus and lung, etc. In particular, hydrochloride may react with herbal aromatic compounds, especially, phenol and phenolic compounds, which are secondarily formed during combustion, to form poisonous dioxins. Therefore, in the present composition, ipecac alkaloid salt or salt of emetine should be converted into basic alkaloid before its use.

For conversion of salt into base, conventional alkaloid extraction method may be employed. That is, in the present invention, general alkaloid fractionation method is used for obtaining fraction, which contains mainly basic alkaloids. Specifically, the given amount of ipecac powder is degreased with hexane, and to the residual plant are added alkalis such as ammonium to basify. Subsequently, the resulting solution is extracted with water-immiscible solvent such as ether, etc. The obtained fraction contains 70–80% of total alkaloids. Further, emetine hydrochloride is dissolved in water and then, extracted with water-immiscible solvent such as ether, etc. to obtain emetine.

Generally, a daily dose of emetine for the halt of coughing and for the discharge of phlegm ranges about 1.0–1.5 mg of emetine hydrochloride. The daily dose of *Radix ipecauanhae* for the same purpose ranges about 0.03–0.15 g, and a single dose thereof for vomiting ranges about 0.5–1.0 g. In the present invention, it is important to adapt the dosage for inducing smoking cessation. That is, *Radix ipecauanhae* contained in the present composition has the practical purpose of nauseating rather than of vomiting and thus, vomiting is conversely regarded as an adverse event. In view of the fact that a single dose of *Radix ipecauanhae* for vomiting is 0.5–1.0 g, its amount for smoking cessation would be lesser than 0.5–1.0 g. Synergic effect with nicotine as described hereunder can lead to remarkable reduction of the inhalation amount of *Radix ipecauanhae*, i.e. alkaloids therefrom. In the present invention, ipecac alkaloid is preferably contained at 0.01 to 2 wt %, more preferably, 0.05 to 0.3 wt %, as basic alkaloid fraction, on the basis of the total weight of the composition. In another aspect, emetine, if employed as active ingredient, is preferably contained at 0.005 to 0.5 wt %, more preferably 0.005 to 0.15 wt %, on the basis of the total weight of the composition. In the present composition, nicotine, if employed as excipient, is contained at the residual amount excluding the active ingredient. For example, in case that the total weight of the composition is 100 g and the content of ipecac alkaloid is 2000 mg, 98 g of tobacco leaf is preferably added thereto.

If desired, the composition of the present invention may contain tobacco leaf having nicotinic ingredient. In the present composition, the tobacco leaf may not only function as excipient but also provide properties inherent in tobacco. Nicotine has complicated and unexpectable mechanism. It functions on various nerve transfer systems and further, stimulates or desensitizes receptor depending upon its dosage. Usually, nicotine inhaled into the body through smoking does not lead to desensitization, but causes stimulation and excitation of receptor. Nicotine displays vomiting effect via the same mechanism as emetine. Mechanism of vomiting in nicotine is as follows: It stimulates vomitive chemoreceptor trigger zone of area postremia in medulla oblongata thereby to activate vagal and spinal afferent which receive vomiting and reflex thereby to promote vomiting.

From the fact that emetine and nicotine pass through many common afferent areas through their reaction mechanism, these two substances are anticipated to have synergic or additive effect. Nicotine in the form of tobacco leaf may be comprised in the present composition at a conventional amount as excipient for the manufacture of tobacco. For example, in case that the total weight of the composition is 100 g and the content of emetine is 500 mg, 99.5 g of tobacco leaf may be contained. Such content of nicotine is sufficient for exhibiting synergic or additive effect.

A further aspect of the present invention is to provide a composition for inducing smoking cessation comprising smokable herbal materials instead of tobacco leaf. In this composition, as the bulk of herbal materials, *Herba adenophorae, Herba centellae, Circii herba* and the like, which contain less herbal phenol, may be employed. *Herba adenophorae*, leaf of *Adenophora triphglla* Var. Japonica, falls within Companulaceae and contains saponins mainly. It is known to be effective for the discharge of phlegm, lung treatment and treatment of pharyngolaryngitis, etc. In addition, *Herba centellae* has the effect of preventing or treating damages in epithelial tissue due to smoking.

Furthermore, the composition of the present invention may contain additional ingredients for providing gustatory, aromatic and sedative effects. Examples of such ingredients include *Herba foeniculi,* Fructus Phyllanthus emblica, *Herba valerianae, Herba leonuri sibiricus,* tobacco flavor, etc. *Herba foeniculi* is added for providing aroma and used as leaf of *Foeniculum vulgaris* of Umbelliferae. Its fruit is known to be useful as aromatic agent and to be effective for treatment of a pain in the abdomen, emmenagogue, low back pain and the like. Its root contains 3–6% of essential oils such as anethole, fenchone, phellandrene, etc. Extract from Fructus Phyllanthus emblica is added not only as gustatory ingredient but also as sedative of throat and bronchus irritated by smoking. It contains 1.0–1.8% of ascorbic acid and gallotannins. The composition may contain *Herba valerianae* for psychological relief. Finally, for disguise the unfamiliar taste of non-tobacco cigarette, *Herba leonuri sibiricus* of the bitter taste and tobacco flavors are added to the composition. *Herba leonuri sibiricus* contains leonuri alkaloids such as leonurine, etc. and is known effective for dysmenorrhoea, abdominal dropsy and for purifying blood and detoxification.

The above-described auxiliary agents may be used at an unlimited amount within the range of desired advantageous effects without any side effects. Such agents may be omitted, or increased or decreased considering smoker's taste. The amount of these agents does not need to be specifically limited, but they are preferably used at the same amount as tobacco leaf. That is, in a preferable embodiment, cigarette is manufactured by mixing 0.01–2 wt % of ipecac basic alkaloid fraction obtained from Preparation 1 or 0.005–0.5 wt % of basic emetine obtained from Preparation 2 as active ingredient with the residual amount of the above auxiliary agents.

Hereunder, a process for preparing the composition of the present invention will be explained. Smoking cessation cigarettes are prepared as follows: Admixing of various concentrations of basic alkaloid fraction from *Radix ipecauanhae* with the given amount of tobacco leaf The alkaloid fraction or emetine is mixed with a commercial cigarette, the weight of which is 0.8–1.0 g excluding filter, at variable amounts. Alkaloid content must be adjusted within the range where it does not cause vomiting substantially regarded as adverse event in view of the purpose of the present invention. A variety of dosages of alkaloids enable to determine optimal dosage in each individual considering smoker's sensitivity.

In the present invention, two approaches are considered for the manufacture of cigarettes. (1) Admixing ipecac basic total alkaloids or emetine with tobacco simultaneously, and (2) manufacturing cigarettes consisting of ipecac basic total alkaloids or emetine, smoking the cigarettes to pre-sensitize chemo-receptor trigger zone and smoking tobacco to induce synergic effect with nicotine after the given time.

BEST MODE FOR CARRYING OUT THE INVENTION

This invention will be better understood from the following examples. However, one skilled in the art will readily appreciate the specific materials and results described are merely illustrative of, and are not intended to, nor should be intended to, limit the invention as described more fully in the claims, which follow thereafter.

Preparation 1: Preparation of Basic Alkaloid Fraction from *Radix ipecauanhae*

1000 g of ipecac powder was introduced into 5000 ml of Soxhlet extractor and was extracted with 2000 ml of hexane for 3 hours. Subsequently, hexane was removed by filtration and the residual hexane was removed from ipecac residue. The ipecac powder was introduced into 5000 ml of Stirring extractor and extracted with 2000 ml of methanol at 40° C. for 5 hours. The extract was filtered and ipecac residue was extracted further twice according to the same procedure. The extracts with methanol were combined and the solvent was removed under reduced pressure to obtain 35 g of the residue. The residue was suspended in 500 ml of water and thereto was added 0.1 N sodium hydroxide to adjust pH to about 7.0–7.5. Then, the suspension was extracted twice with 500 ml of ether and filtered to obtain liquid extract with ether. The extract was washed twice with 100 ml of water and dried to obtain 18 g of alkaloid fraction (total alkaloid fraction). The fraction was analyzed, according to the procedure described in the literature Deutsches Arzneibuch 9, Ausgabe 1986 and as a result, identified to have 80% of total alkaloids.

Preparation 2: Preparation of Emetine from Emetine Dihydrochloride 5 g of Emetine dihydrochloride ($5H_2O$) was dissolved in 100 ml of water and thereto was added 0.1 N sodium hydroxide to adjust pH to 7.5. The solution was extracted three times with 100 ml of ether. The removal of ether gave about 4 g of emetine (emetine).

EXAMPLE 1

10 mg of the total alkaloid fraction obtained from Preparation 1 was dissolved in 10 ml of 40% ethanol. The solution was sprayed into 100 g of tobacco for commercial cigarette and then, mixed. The total moisture content of the mixture was adjusted to 10–12%. 100 cigarettes were manufactured using this mixture.

EXAMPLES 2 TO 18

Cigarettes of the following Examples 2 to 18 were manufactured according to the substantially same method as in Example 1 except that alkaloid fraction and ethanol were used as shown in the following Table 1.

TABLE 1

| Examples | Alkaloid content (mg) | Ethanol content (ml) |
|---|---|---|
| 2 | 20 | 10 |
| 3 | 40 | 10 |
| 4 | 60 | 10 |
| 5 | 100 | 15 |
| 6 | 150 | 10 |
| 7 | 200 | 20 |
| 8 | 250 | 20 |
| 9 | 300 | 20 |
| 10 | 400 | 25 |
| 11 | 500 | 30 |
| 12 | 600 | 30 |
| 13 | 700 | 30 |
| 14 | 800 | 30 |
| 15 | 900 | 30 |
| 16 | 1000 | 30 |
| 17 | 1500 | 30 |
| 18 | 2000 | 30 |

EXAMPLE 19

5 mg of emetine obtained from Preparation 2 was dissolved in 2 ml of 40% ethanol. The solution was sprayed into 100 g of tobacco for commercial cigarette and then, mixed. The moisture content of the mixture was adjusted to about 10–12% to manufacture 100 cigarettes.

EXAMPLES 20 TO 30

Cigarettes of the following Examples 20 to 30 were manufactured according to the substantially same method as in Example 19 except that emetine and ethanol were used as shown in the following Table 2.

TABLE 2

| Examples | Emetine content (mg) | Ethanol content (ml) |
|---|---|---|
| 20 | 10 | 2 |
| 21 | 20 | 2 |
| 22 | 50 | 10 |
| 23 | 100 | 10 |
| 24 | 130 | 10 |
| 25 | 150 | 15 |
| 26 | 200 | 20 |
| 27 | 250 | 20 |
| 28 | 300 | 20 |
| 29 | 400 | 30 |
| 30 | 500 | 30 |

Preparation 3: Preparation of Extract from Fructus Phyllanthus emblica 1000 g of Fructus Phyllanthus emblica was introduced into 5000 ml of stirring extractor and extracted three times with 3000 ml of 95% ethanol. The extract with ethanol was concentrated by evaporation and the residual extract was used as is.

Preparation 4: Slicing of Raw Materials and Adjustment of Moisture

*Herba adenophorae, Herba leonuri, Herba foeniculi, Folia valerianae, Herba centellae* and *Circii herba* with the moisture content of about 20% were sliced by tobacco slicer and then, dried to have the moisture content of about 5%.

Preparation 5: Preparation of Raw Mixtures 1, 2 and 3

*Herba adenophorae* (50 g), *Herba leonuri* (15 g), *Herba foeniculi* (5 g) and *Folia valerianae* (1 g) in Preparation 4, tobacco flavor (10 mg), and extract from Fructus Phyllanthus emblica(5 g) in Preparation 3 were mixed to obtain raw mixture 1. *Herba adenophorae* (25 g), *Herba centellae* (25 g), *Herba leonuri* (15 g), *Herba foeniculi* (5 g) and *Folia valerianae* (1 g) in Preparation 4, tobacco flavor (10 mg), and extract from Fructus Phyllanthus emblica (5 g) in Preparation 3 were mixed to obtain raw mixture 2. *Herba adenophorae* (25 g), *Circii herba* (25 g), *Herba leonuri* (15 g), *Herba foeniculi* (5 g) and *Folia valerianae* (1 g) in Preparation 4, tobacco flavor (10 mg), and extract from Fructus Phyllanthus emblica (5 g) in Preparation 3 were mixed to obtain raw mixture 3.

EXAMPLE 31

10 mg of total alkaloid fraction obtained from Preparation 1 was dissolved in 2 ml of 40% ethanol. The solution was sprayed into raw mixture 1 in Preparation 5 and then, well blended. The blend was dried to evaporate ethanol and the moisture content was adjusted to 10–12%. Using this, 76 cigarettes were manufactured.

EXAMPLES 32 to 58

Cigarettes of the following Examples 32 to 58 were manufactured according to the substantially same method as in Example 31 except that alkaloid fraction, ethanol and raw structure were used as shown in the following Table 3.

TABLE 3

| Example | Alkaloid content (mg) | Ethanol content (ml) | Raw mixture of Preparation 5 |
|---|---|---|---|
| 32 | 20 | 2 | 1 |
| 33 | 40 | 10 | 1 |
| 34 | 60 | 10 | 1 |
| 35 | 100 | 15 | 1 |
| 36 | 150 | 15 | 1 |
| 37 | 200 | 15 | 1 |
| 38 | 250 | 15 | 1 |
| 39 | 300 | 15 | 1 |
| 40 | 10 | 2 | 2 |
| 41 | 15 | 2 | 2 |
| 42 | 20 | 2 | 2 |
| 43 | 40 | 10 | 2 |
| 44 | 60 | 10 | 2 |
| 45 | 100 | 15 | 2 |
| 46 | 150 | 15 | 2 |
| 47 | 200 | 15 | 2 |
| 48 | 250 | 15 | 2 |
| 49 | 300 | 15 | 2 |
| 50 | 10 | 2 | 3 |
| 51 | 20 | 2 | 3 |
| 52 | 40 | 10 | 3 |
| 53 | 60 | 10 | 3 |
| 54 | 100 | 15 | 3 |
| 55 | 150 | 15 | 3 |
| 56 | 200 | 15 | 3 |
| 57 | 250 | 15 | 3 |
| 58 | 300 | 15 | 3 |

EXAMPLE 59

10 mg of emetine obtained from Preparation 2 was dissolved in 2 ml of 40% ethanol. The solution was sprayed into raw mixture 1 obtained from Preparation 5 and then mixed. The mixture was allowed to stand at room temperature to remove ethanol. The moisture content was adjusted to about 10–12% to manufacture 76 cigarettes.

EXAMPLES 60 to 82

Cigarettes of the following Examples 60 to 82 were manufactured according to the substantially same method as in Example 59 except that emetine, ethanol and raw mixture were used as shown in the following Table 4.

TABLE 4

| Example | Emetine content (mg) | Ethanol content (ml) | Raw mixture of Preparation 5 |
|---|---|---|---|
| 60 | 20 | 2 | 1 |
| 61 | 50 | 2 | 1 |
| 62 | 70 | 10 | 1 |
| 63 | 100 | 10 | 1 |
| 64 | 130 | 10 | 1 |
| 65 | 150 | 15 | 1 |
| 66 | 200 | 20 | 1 |
| 67 | 250 | 20 | 1 |
| 68 | 300 | 20 | 1 |
| 69 | 400 | 30 | 1 |
| 70 | 500 | 30 | 1 |
| 71 | 10 | 2 | 2 |
| 72 | 20 | 2 | 2 |
| 73 | 50 | 2 | 2 |
| 74 | 70 | 10 | 2 |
| 75 | 100 | 10 | 2 |
| 76 | 130 | 10 | 2 |
| 77 | 150 | 15 | 2 |
| 78 | 200 | 20 | 2 |
| 79 | 250 | 20 | 2 |
| 80 | 300 | 20 | 2 |
| 81 | 400 | 30 | 2 |
| 82 | 500 | 30 | 2 |

Preparation 6: Preparation of Raw Mixtures 4, 5 and 6

Raw mixtures were prepared in the same manner as in Preparation 5 excluding *Fructus Phyllanthus emblica*. Specifically, *Herba adenophorae* (50 g), *Herba leonuri* (15 g), *Herba foeniculi* (5 g) and *Folia valerianae* (1 g) in Preparation 4, and tobacco flavor (10 mg) were mixed to obtain raw mixture 4. *Herba adenophorae* (25 g), *Herba centellae* (25 g), *Herba leonuri* (15 g), *Herba foeniculi* (5 g) and *Folia valerianae* (1 g) in Preparation 4, and tobacco flavor (10 mg) were mixed to obtain raw mixture 5. *Herba adenophorae* (25 g), *Circii herba* (25 g), *Herba leonuri* (15 g), *Herba foeniculi* (5 g) and *Folia valerianae* (1 g) in Preparation 4, and tobacco flavor (10 mg) were mixed to obtain raw mixture 6.

EXAMPLE 83

10 mg of total alkaloid fraction obtained from Preparation 1 was dissolved in 2 ml of 40% ethanol. The solution was sprayed into raw mixture 4 in Preparation 6 and then, well blended. The blend was dried to evaporate ethanol and the moisture content was adjusted to 10–12%. Using this, 76 cigarettes were manufactured.

EXAMPLES 84 TO 109

Cigarettes of the following Examples 84 to 109 were manufactured according to the substantially same method as in Example 83 except that alkaloid fraction, ethanol and raw mixture were used as shown in the following Table 5.

TABLE 5

| Example | Alkaloid content (mg) | Ethanol content (ml) | Raw mixture of Preparation 5 |
|---|---|---|---|
| 84 | 20 | 2 | 4 |
| 85 | 40 | 10 | 4 |
| 86 | 60 | 10 | 4 |
| 87 | 100 | 15 | 4 |
| 88 | 150 | 15 | 4 |
| 89 | 200 | 15 | 4 |

TABLE 5-continued

| Example | Alkaloid content (mg) | Ethanol content (ml) | Raw mixture of Preparation 5 |
|---|---|---|---|
| 90 | 250 | 15 | 4 |
| 91 | 300 | 15 | 4 |
| 92 | 10 | 2 | 5 |
| 93 | 20 | 2 | 5 |
| 94 | 40 | 10 | 5 |
| 95 | 60 | 10 | 5 |
| 96 | 100 | 15 | 5 |
| 97 | 150 | 15 | 5 |
| 98 | 200 | 15 | 5 |
| 99 | 250 | 15 | 5 |
| 100 | 300 | 15 | 5 |
| 101 | 10 | 2 | 6 |
| 102 | 20 | 2 | 6 |
| 103 | 40 | 10 | 6 |
| 104 | 60 | 10 | 6 |
| 105 | 100 | 15 | 6 |
| 106 | 150 | 15 | 6 |
| 107 | 200 | 15 | 6 |
| 108 | 250 | 15 | 6 |
| 109 | 300 | 15 | 6 |

Experiment

The composition of the present invention was tested for its smoking cessation inducing effect on 40 healthy men and women having no particular disease. 40 persons were randomly selected among volunteers who agreed to participate in smoking cessation program and provided with smoking cessation program. The volunteers were divided into 2 groups according to double blind test. One group were provided with smoking cessation-inducing cigarettes (cigarettes of Example 4) (active treatment group) and the other were provided with conventional cigarettes containing nicotine (placebo group). Before starting smoking cessation program, individuals were inquired of their smoking disposition and based thereon, provided with the required amount of smoking cessation-inducing cigarettes. The volunteers were checked for their smoking disposition once a week for 6 weeks. The results are shown in the following Table 6.

TABLE 6

Desire for smoking cessation by the lapse of time

| | No. of persons ceasing smoking by the lapse of time (week) | | | | | | |
|---|---|---|---|---|---|---|---|
| | 1 | 2 | 3 | 4 | 5 | 6 | Total |
| Active treatment group | 4 | 4 | 3 | 1 | 0 | 0 | 12/20 |
| Placebo group | 2 | 1 | 1 | 0 | 0 | 0 | 4/20 |

As shown above, in placebo group, only 20% of the volunteers had no desire for smoking after 6 weeks. In comparison, 60% of the volunteers in active treatment group did not have the desire for smoking. Those who succeeded to quit smoking did not show withdrawal symptom, uneasiness or change of emotion.

INDUSTRIAL APPLICABILITY

According to the present invention, smokers became nausea or state of repulsion to tobacco and finally lead to cease smoking, by co-administration of emetine of much less than dosage for medical purpose and a conventional inhalation amount of nicotine, or by pre-administration of emetine followed by smoking tobacco after the given time. Accordingly, the use of the present composition enables to diminish the craving for smoking without any particular side effect.

What is claimed is:

1. A composition for inducing smoking cessation comprising as active ingredient basic alkaloid fraction from *Radix ipecauanhae* or basic emetine, wherein the content of the basic alkaloid fraction ranges from 0.05 to 0.3 wt %, or the content of basic emetine ranges from 0.005 to 0.5 wt %, based on the total weight of the composition.

2. The composition according to claim 1, wherein the content of basic emetine ranges from 0.005 to 0.15 wt %, based on the total weight of the composition.

3. The composition according to claim 1 further comprising one or more auxiliary agents selected from the group consisting of *Nicotiana tabacum*, Fructus Phyllanthus emblica, *Herba adenophorae*, *Herba leonuri*, *Herba foeniculi*, *Folia valerianae*, *Herba centellae* and *Circii herba*.

4. A method for inducing smoking cessation comprising the steps of smoking a composition obtained by admixing the composition according to claim 1 with tobacco leaf, or smoking the composition according to claim 1 while stimulating chemo-receptor trigger zone followed by smoking tobacco thereafter.

5. A composition comprising:
  (1) a smokable herbal material other than tobacco leaf, and/or tobacco leaf; and
  (2) a smoking cessation inducing effective amount of the composition according to claim 1.

6. The composition according to claim 5, wherein said smokable herbal material is at least one selected from the group consisting of *Herba adenophorae*, *Herba centellae*, *Circii herba*, *Herba foeniculi*, Fructus Phyllanthus emblica, *Herba valerianae*, and *Herba leonuri sibiricus*.

7. A cigarette comprising the composition according to claim 6.

8. A method for inducing smoking cessation, comprising:
  smoking a composition according to claim 1; and
  smoking tobacco thereafter.

9. A method for inducing smoking cessation, comprising:
  smoking a composition according to claim 5.

10. The composition according to claim 1, wherein said composition contains no acidic alkaloid fraction from *Radix ipecauanhae* or no emetine hydrochloride.

11. The composition according to claim 1, wherein said active ingredient is basic alkaloid fraction from *Radix ipecauanhae*.

12. The composition according to claim 1, wherein said active ingredient is basic emetine.

* * * * *